US012593975B2

(12) United States Patent (10) Patent No.: US 12,593,975 B2
Boutinon et al. (45) Date of Patent: Apr. 7, 2026

(54) SYSTEM AND METHOD FOR DETERMINING REFRACTION FEATURES OF BOTH FIRST AND SECOND EYES OF A SUBJECT

(71) Applicant: Essilor International, Charenton-le-Pont (FR)

(72) Inventors: Stephane Boutinon, Charenton-le-Pont (FR); Estelle Netter, Charenton-le-Pont (FR); Martha Hernandez-Castaneda, Charenton-le-Pont (FR); Konogan Baranton, Charenton-le-Pont (FR); Gildas Marin, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 927 days.

(21) Appl. No.: 17/785,780

(22) PCT Filed: Dec. 15, 2020

(86) PCT No.: PCT/EP2020/086278
§ 371 (c)(1),
(2) Date: Jun. 15, 2022

(87) PCT Pub. No.: WO2021/122640
PCT Pub. Date: Jun. 24, 2021

(65) Prior Publication Data
US 2023/0053457 A1 Feb. 23, 2023

(30) Foreign Application Priority Data
Dec. 16, 2019 (EP) ..................................... 19306653

(51) Int. Cl.
A61B 3/032 (2006.01)
A61B 3/00 (2006.01)
A61B 3/08 (2006.01)

(52) U.S. Cl.
CPC ............ *A61B 3/032* (2013.01); *A61B 3/0033* (2013.01); *A61B 3/005* (2013.01); *A61B 3/08* (2013.01)

(58) Field of Classification Search
CPC ...... A61B 3/08; A61B 3/028; G02B 27/0025; G02B 30/10; G02B 27/0172;
(Continued)

(56) References Cited

U.S. PATENT DOCUMENTS

2013/0135299 A1 5/2013 Park et al.
2014/0327750 A1 11/2014 Malachowsky et al.
(Continued)

FOREIGN PATENT DOCUMENTS

JP 2015/504641 A 2/2015
JP 2016/145956 A 8/2016
(Continued)

OTHER PUBLICATIONS

Chinese Office Action and Search Report issued Mar. 17, 2025 in Chinese Patent Application No. 202080086191.1 (with unedited computer-generated English translation), 17 pages.
(Continued)

*Primary Examiner* — William R Alexander
*Assistant Examiner* — Mackenzi Waddell
(74) *Attorney, Agent, or Firm* — Oblon, McClelland, Maier & Neustadt, L.L.P.

(57) ABSTRACT

A system for determining refraction features of both first and second eyes of a subject including a light field display device, a system of localization of the positions of the first and second eyes of the subject, the light field display device generating a first light field directed selectively toward the first eye, and, respectively, a second light field directed selectively toward the second eye, control circuitry that adjusts the first light field as a function of at least a first
(Continued)

refraction parameter associated with at least a first optical aberration for the first eye and the control circuitry adjusting said second light field as a function of at least a second refraction parameter associated with at least a second optical aberration for the second eye.

20 Claims, 4 Drawing Sheets

(58) Field of Classification Search
CPC ...... G02B 2027/0138; G02B 2027/014; G02B 27/0093
USPC .......................................................... 351/237
See application file for complete search history.

(56) References Cited

U.S. PATENT DOCUMENTS

| | | | | |
|---|---|---|---|---|
| 2014/0327771 | A1* | 11/2014 | Malachowsky .... | G02B 27/0075 348/148 |
| 2015/0374224 | A1* | 12/2015 | Baranton ............... | A61B 3/103 351/246 |

| | | | | |
|---|---|---|---|---|
| 2016/0042501 | A1 | 2/2016 | Huang et al. | |
| 2016/0223817 | A1 | 8/2016 | Kizu et al. | |
| 2017/0055825 | A1* | 3/2017 | Tumlinson ........... | A61B 3/0025 |
| 2017/0060399 | A1 | 3/2017 | Hough et al. | |
| 2018/0136486 | A1* | 5/2018 | Macnamara ............. | A61B 3/00 |
| 2019/0082168 | A1 | 3/2019 | Lee et al. | |
| 2019/0246889 | A1 | 8/2019 | Marin et al. | |
| 2020/0069174 | A1 | 3/2020 | Marin et al. | |

FOREIGN PATENT DOCUMENTS

| | | |
|---|---|---|
| JP | 2019/54513 A | 4/2019 |
| JP | 2019/531769 A | 11/2019 |
| WO | WO 2018/022521 A1 | 2/2018 |
| WO | WO 2018/104600 A1 | 6/2018 |

OTHER PUBLICATIONS

International Search Report issued Jan. 18, 2021, in PCT/EP2020/086278 filed Dec. 15, 2020, 2 pages.
Office Action issued Mar. 18, 2024, in corresponding Japanese Patent Application No. 2022-536830 (with English Translation), 13 pages.

* cited by examiner

Fig.1
2D
Prior Art
Fig.2
3D
Prior Art
Fig.3
4D
Prior Art
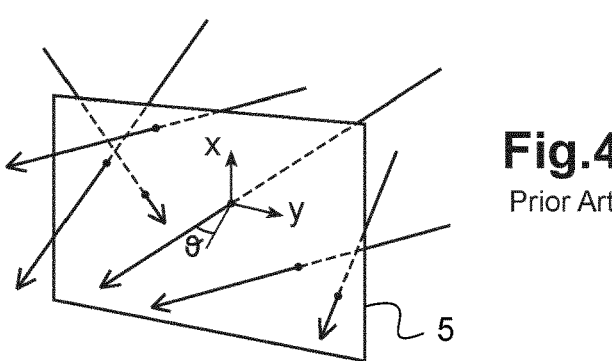
Fig.4
Prior Art
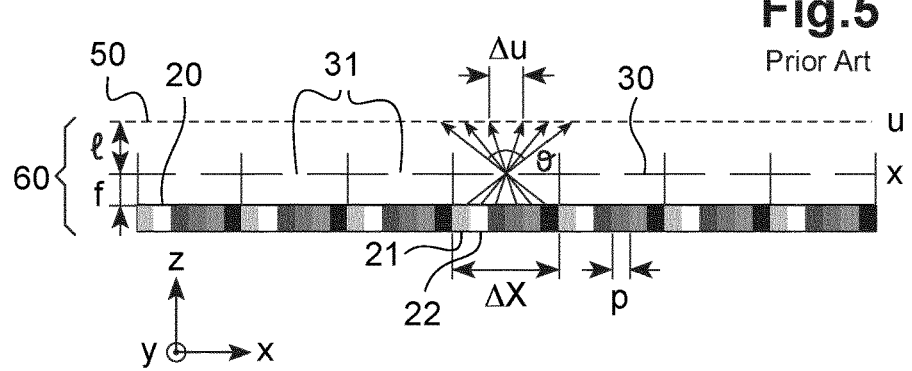
Fig.5
Prior Art
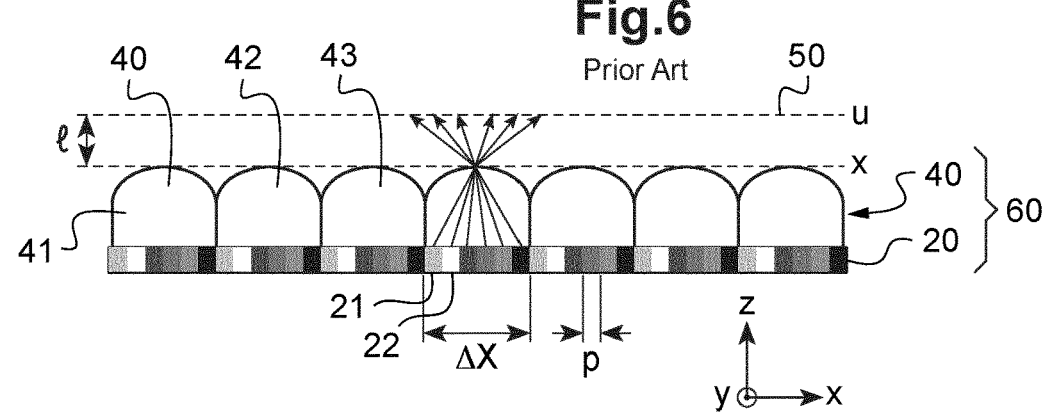
Fig.6
Prior Art An image of a
visual stimulus

Fig.10
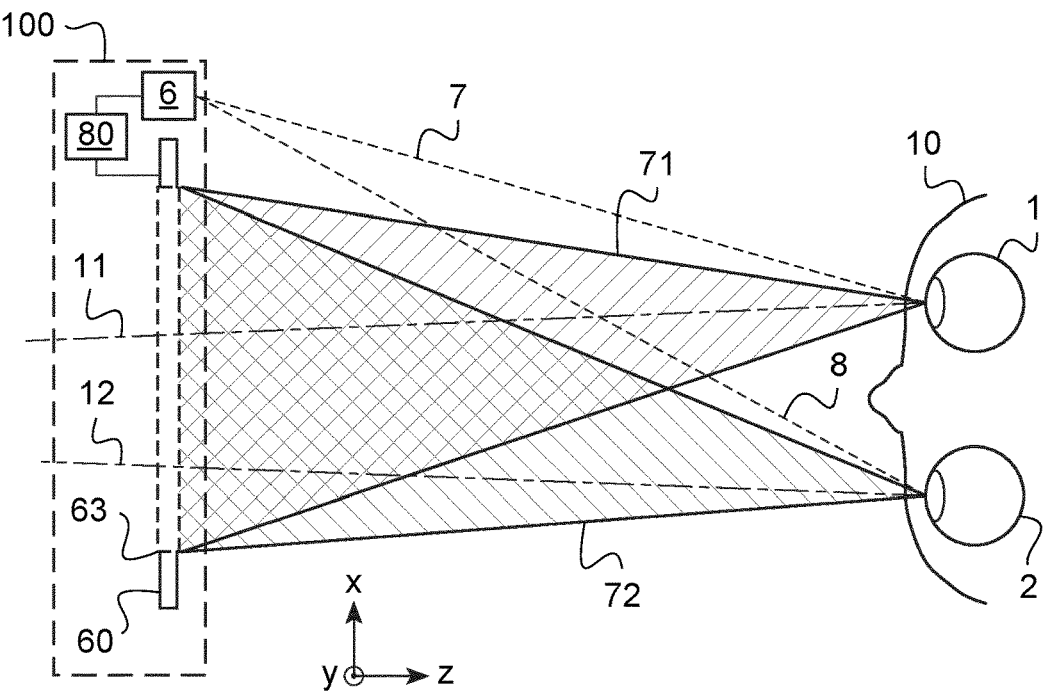
Fig.11
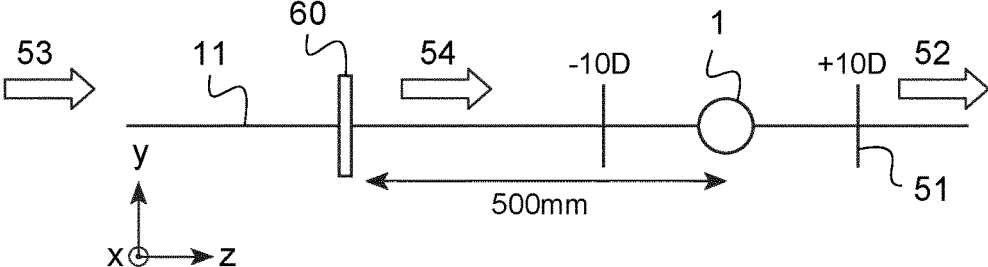
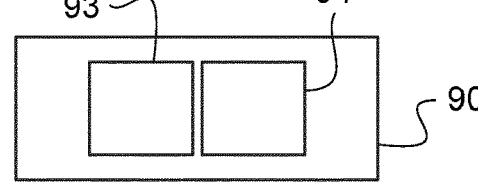
Fig.12
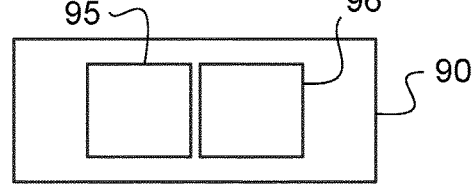
Fig.13

SYSTEM AND METHOD FOR DETERMINING REFRACTION FEATURES OF BOTH FIRST AND SECOND EYES OF A SUBJECT

TECHNICAL FIELD OF THE INVENTION

The invention relates to a system and method for determining refraction correction of the eyes of a subject.

BACKGROUND INFORMATION AND PRIOR ART

Numerous documents describe devices and methods for determining objectively or subjectively refraction features of the eyes of a subject in monocular or binocular vision conditions.

Objective refraction is usually obtained using a skiascope or an auto-refractometer. Objective refraction enables to determine quickly the approximate correction for an individual.

However, subjective refraction is the method of choice to determine the best refraction correction needed by a subject. Conventional subjective refraction is obtained using a set of trial lenses and a trial frame or using a phoropter with a manual or automatic lens changer. These devices generally use lenses of varying optical power by steps of 0.25 diopter (D). The Essilor phoropter vision R800 uses an active optical lens enabling continuous optical power variation.

Document WO 2018/104600 (Essilor Int.) discloses a phoropter for measuring, with high resolution, subjective spherical and/or cylindrical ocular refraction of an eye. The phoropter comprises a conventional refractive optical system combined with a display device, the refractive optical system having an optical power varying by a minimum step and the display device, comprising for example a light field display device, being adapted for varying its optical power by less than the determined minimum step.

Other documents disclose systems based on light field display devices for providing correction of a previously determined vision defect.

For example, document US 2017/0060399 discloses a vision correction system based on a graphical user interface and graphical display that displays a corrected image at least partially compensating for a subject's reduced visual acuity. However, such a system does not provide accurate refraction measurements. Document US 2016/0042501 A1 also discloses a vision correcting display with aberration compensation, based on previously determined optical aberrations parameters of the viewer to compute an aberration-compensated image displayed using a light-field element. Document WO 2018/091984 A1 discloses a near-eye sequential light-field projector which projects a sequence of light field components into each eye of the viewer forming always-in-focus retinal images, so that the viewer perceives monocular depth cues, providing the illusion of depth. Documents US 2014/0327750 and US 2014/0327771 disclose systems and methods for displaying a scene as a light field.

However, these documents do not disclose a method or apparatus for measuring precisely ocular refraction of a subject, in particular in binocular vision, or for correcting refraction of the viewer.

Having binocular well corrected images is indeed important to provide accurate refraction measurement, since monocular refraction may lead to accommodation, and binocular refraction without differentiating right eye and left eye refraction does not address anisometropia (or binocular disparity between the two eyes) that are very frequent.

Thus, there is a need for a system and method enabling accurate subjective determination of refraction correction of each eye in binocular vision conditions, so as to provide him/her with the most comfortable vision correction, and without the use of additional lenses.

SUMMARY OF THE INVENTION

Therefore one object of the invention is to provide a system for determining refraction features of both first and second eyes of a subject, the system comprising a light field display device having a referential in three-dimensions, a system of localisation of the positions of the first and second eyes of the subject viewing said light field display device, relatively to the referential, a control unit to drive the light field display device, the light field display device being configured to generate a first light field directed selectively toward the first eye of the subject, said first light field being adapted to form a first image on the first eye of the subject, the control unit being adapted to adjust said first light field as a function of at least a first refraction parameter associated with at least a first optical aberration for said first eye so that said first image is perceived corrected for a first adjusted value of said first refraction parameter by the first eye, the control unit being adapted to determine a refraction feature of the first eye from the first adjusted value of said first refraction parameter and the light field display device is configured to generate a second light field directed selectively toward the second eye of the subject, said second light field being adapted to form a second image on said second eye of the subject, the control unit being adapted to adjust said second light field as a function of at least a second refraction parameter associated with at least a second optical aberration for the second eye so that the second image is perceived corrected for a second adjusted value of said second refraction parameter by the second eye, the control unit being adapted to determine a refraction feature of the second eye from the second adjusted value of said second refraction parameter.

The system based on a light field display device enables to determine refraction features of both first and second eyes of a subject, in monocular or binocular vision, without the use of additional lenses and without mechanically moving part.

According to some embodiments, the light field display device comprises a single screen, the first light field and the second light field being generated from a same area, with sequential alternation, or from two distinct areas of the light field display device.

According to another embodiment, the light field display device comprises a first screen adapted to generate the first light field directed selectively toward said first eye of the subject and a second screen adapted to generate the second light field directed selectively toward the second eye of the subject.

According to a particular and advantageous aspect, the system comprises a user interface adapted to record a first response of the subject relative to a first sharpness of the first image perceived by the first eye and a second response of the subject relative to a second sharpness of the second image perceived by the second eye, and the control unit is adapted to adjust respectively said first and second light fields as a function of said first and second responses recorded.

In a particular embodiment, the user interface is adapted to enter values of said first and second refraction parameters, and the control unit is adapted to adjust respectively said first and second light fields as a function of said first and second refraction parameters values entered.

According to another particular aspect, the system comprises means to occlude selectively the first light field toward the second eye and/or to occlude selectively the second light field toward the first eye.

According to still another particular aspect, the light field display device comprises a digital display comprising an array of pixels and a parallax barrier mask layered on the array of pixels, or a multi-layered liquid crystal display device.

The parallax barrier mask may be selected among an array of pinholes, a lenslet array, a micro-lens array, a lenticular array and a lenticular lens.

According to another aspect, the light field display device comprises a liquid crystal display (LCD) with directive backlight illumination.

According to another aspect, the system of localisation comprises an eyetracker, a 3D scanning device, a camera, a time-of-flight sensor and/or a pupil-size measuring device.

The system of localisation may be adapted to determine a pupil diameter and/or an eye gaze direction.

According to an embodiment, the first light field and the second light field are predetermined so that the first image and the second image comprise at least one common visual stimulus enabling fusion of the first image and the second image by the subject.

A further object of the invention is to provide a method for determining a refraction feature of both eyes of a subject, the method comprising the following steps:

a) localising the position of a first eye and the position of a second eye of the subject relatively to a three-dimensions referential of a light field display device;

b) using the light field display device for generating a first light field directed selectively toward the first eye of the subject, said first light field being adapted to form a first image on said first eye of the subject;

c) adjusting the first light field as a function of at least a first refraction parameter associated with at least a first optical aberration of the first eye so that said first image is perceived corrected for a first adjusted value of said first refraction parameter by the first eye;

d) determining a refraction feature of the first eye from the first adjusted value of said first refraction parameter;

e) using the light field display device for generating a second light field directed selectively toward the second eye of the subject, said second light field being adapted to form a second image on the second eye of the subject;

f) adjusting the second light field as a function of at least a second refraction parameter associated with at least a second optical aberration of the second eye so that the second image is perceived corrected for a second adjusted value of said second refraction parameter by the second eye;

g) determining a refraction feature of the second eye from the second adjusted value of said second refraction parameter.

According to a particular aspect, the steps b) to c) and, respectively, the steps e) to f) are performed sequentially in time and during steps b) to c) the second light field is off or occluded toward the second eye and during steps e) to f) the first light field is off or occluded toward the first eye.

According to another particular aspect, the steps b) to c) and, respectively, the steps e) to f) are performed simultaneously.

In an embodiment, the method comprises a run according to claim 12 for the first eye in monocular vision and another run according to claim 12 for the second eye in monocular vision and a run according to claim 13 simultaneously for the first eye and the second eye in binocular vision.

According to a particular embodiment, the method further comprising the steps:

h) recording a first response of the subject relative to a first sharpness of the first image perceived by the first eye, and i) recording a second response of the subject relative to a second sharpness of the second image perceived by the second eye, and during step c) the first light field is adjusted as a function of said first response recorded during step h), and during step f) the second light field is adjusted as a function of said second response recorded during step i).

According to a particular aspect, the refraction feature(s) to be determined comprises sphere, cylinder and axis, addition values and/or high order aberrations for the first eye and for the second eye of the subject in monocular and/or binocular conditions.

According to another particular aspect, the first light field and the second light field are predetermined so that the first image and the second image have at least one common feature enabling fusion of the first image and the second image when seen by the subject.

According to still another particular aspect, the first light field is displayed at a first distance from the first eye and the second light field is displayed at a second distance from the second eye, the first distance and the second distance being adjusted as a function of inter-pupillary distance between the first eye and the second eye.

BRIEF DESCRIPTION OF THE DRAWINGS

The following description with reference to the accompanying drawings will make it clear what the invention consists of and how it can be achieved. The invention is not limited to the embodiments illustrated in the drawings. Accordingly, it should be understood that where features mentioned in the claims are followed by reference signs, such signs are included solely for the purpose of enhancing the intelligibility of the claims and are in no way limiting on the scope of the claims.

Reference is now made to the brief description below, taken in connection with the accompanying drawings and detailed description, wherein like reference numerals represent like parts.

In the accompanying drawings:

FIG. 1 shows the light properties of a conventional 2D image;

FIG. 2 shows the light properties of a 3D light field;

FIG. 3 shows the light properties of a 4D light field;

FIG. 4 shows the light properties of another 4D light field;

FIG. 5 shows a side view of a first type of light field display device according to the prior art;

FIG. 6 shows a side view of a second type of light field display device according to the prior art;

FIG. 7 illustrates schematically a top view of a first embodiment of a system for determining refraction features of the eyes of a subject;

FIG. 8 illustrates schematically an exemplary system according to the first embodiment;

FIG. 9 shows an image of a visual stimulus as seen by the subject;

FIG. 10 illustrates schematically a top view of a second embodiment of a system for determining refraction features of the eyes of a subject;

FIG. 11 illustrates an exemplary method for searching the sphere according to the present disclosure;

Figure 7:
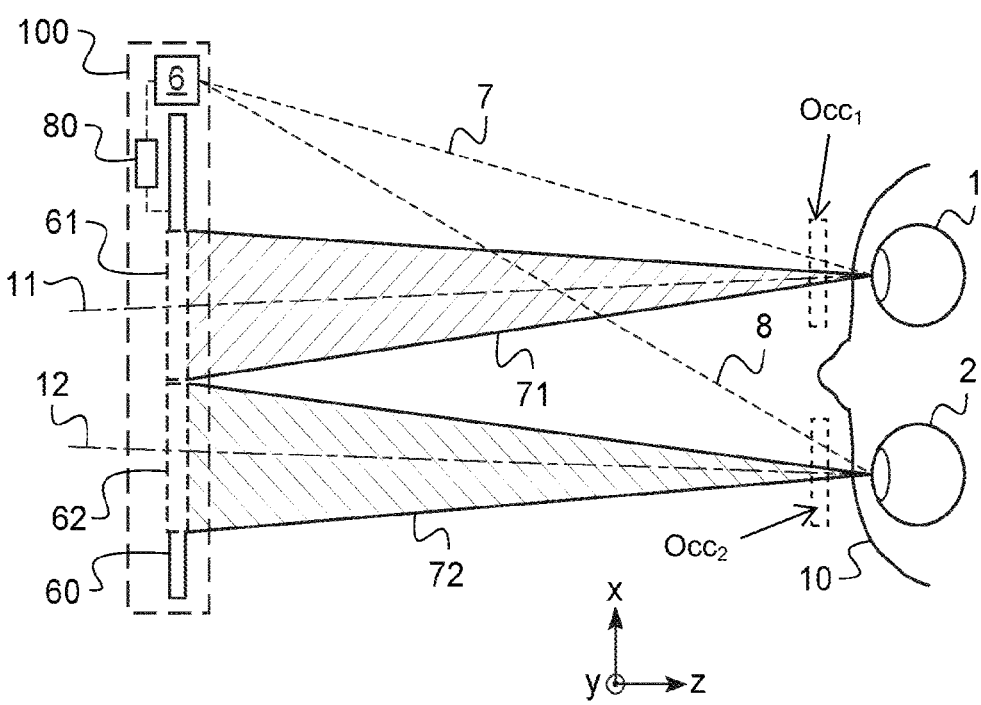

FIG. 12 shows two images generated in a method for determining axis of astigmatism according to the present disclosure;

FIG. 13 shows two images generated in a method for determining axis and cylinder of astigmatism according to the present disclosure.

DETAILED DESCRIPTION OF THE INVENTION

In the description which follows the drawings are not necessary to scale and certain features may be shown in generalized or schematic form in the interest of clarity and conciseness or for informational purposes. In addition, although making and using various embodiments are discussed in detail below, it should be appreciated that as described herein are provided many inventive concepts that may be embodied in a wide variety of contexts. Embodiments discussed herein are merely representative and do not limit the scope of the invention. It will also be obvious to one skilled in the art that all the technical features that are defined relative to a process can be transposed, individually or in combination, to a device and conversely, all the technical features that are defined relative to a device can be transposed, individually or in combination, to a process.

The present disclosure relies on the use of light field display technology to perform subjective refraction exam of a subject's eyes, without the use of a set of additional lenses, as in a conventional phoropter.

Definitions

In the present document, a light field (LF) is a vector function that describes the amount of light flowing in every direction through every point in space. The amount of light is for example the luminance (cd/m$^2$) that represents the power of light by unity of surface and solid angle.

Light field display devices (LFD) are a new type of display that is arriving on the market.

Conventional display devices generate 2D images, wherein the light properties depend on the position (x, y) of each point in the image 3 (see FIG. 1).

In contrast, light field display devices (or LFD) generate a light field and enable to control the amount of light, not only as a function of the position (X, Y), but also as a function of at least one direction. Some light field display devices generate a 3D light field, wherein the amount of light depends on the position (x, y) in the image 4 and on one direction (u) (see FIG. 2). Generating a 3D light field (x, y, u) is also called 1D integral imaging. Other light field display devices generate a 4D light field, wherein the amount of light depends on the position (x, y) in the image 5 and on two transverse directions (u, v) (see FIG. 3). In general, the direction of the vector u is in a horizontal plane and the direction of the vector v is in a vertical plane. Generating a 4D light field (x, y, u, v) is also called integral imaging. Light field display devices can generally control the position and the direction of the light rays for each color (for example RGB or red-blue-green in display devices based on the three colours).

Ideally, a light field display device is like a window and enables to transmit light rays from each point of the image 5 in independent directions (see FIG. 4).

Different kinds of light field display devices are available.

FIG. 5 shows a side view of a known light field display device 60 comprising a high resolution display panel 20 and a parallax barrier 30. The display panel 20 comprises pixels 21, 22 . . . which can be addressed individually. The display panel 20 may include a line of pixels, or, more generally, a 2D array of pixels. In the example illustrated on FIG. 5, the pixels are positioned with a constant pitch, noted p, along axis X, in an orthogonal reference system (X, Y, Z). As illustrated on FIG. 5, the parallax barrier 30 comprises a plate, arranged parallel to the surface of the display panel, and at a distance noted f from the surface of the display panel 20. The plate comprises a plurality of pinholes 31, or microholes, arranged with a pitch, noted Δx, along axis X. Generally the pitch p of the pixels is much smaller than the pitch Δx of the pinhole array. As a function of the pixel which is addressed, the light field passing through the pinhole has a specific vector u relatively to the normal to the display panel 20. As a result, the LFD 60 generates a 3D light field everywhere in a semi-space above the micro-holes 31. FIG. 5 shows an image plane 50 parallel to the light field display device 60, at a distance l from the parallax barrier 30. The image plane 50 is used for 4D representation of a of a light field beam. Each light field beam may be represented by a set four coordinates (x, y, u, v) wherein (x,y) represent the coordinates in the plane of the micro-holes and (u,v) the coordinates in the plane 50 at distance l. The light field generated depends on the position of the pixel which is activated. In the plane 50, the distance Δu between two light rays generated by adjacent pixels passing through the same pinhole depends on the pixels pitch p and on the distance f between the display panel and the parallax barrier. Also, the maximum aperture of the light field has an angle $\theta_{MAX}$ which depends on the pinhole pitch Δx and on the distance f. This angle $\theta_{MAX}$ is determined using the following formula:

$$\tan\theta = \frac{n * p}{f} = \frac{u - x}{l}$$

And $$\frac{\Delta u}{l} = \frac{p}{f}$$

Wherefrom is deduced $$\tan\theta_{MAX} = \frac{\Delta x}{2f}$$

Other kinds of parallax barrier 30 can be used instead of the pinholes array. For example, the LF may be projected directly in the pupil of the eye, by creating virtual pinholes. Each virtual pinhole is associated with a specific source switched on individually. For each virtual pinhole all the directions are driven by a spatial light modulator (SLM).

FIG. 6 shows a side view of another known light field display device 60 comprising a high resolution display panel 20 combined with a lenslet array 40. The lenslet array 40 comprises an array of microlenses 41, 42, 43 . . . placed in near proximity of the display panel 20. For instance, the lenslet array 40 is arranged on top of the display panel 20. The pitch between microlenses is noted Δx, along axis X. As a function of the pixel 21 which is addressed, the light field passing through the microlens 44 has a specific vector u. As a result, the LFD 60 generates a 3D light field in an image plane 50 parallel to the LFD, at a distance l from the lenslet array 40. The light field generated depends on the position of the pixel which is activated.

Of course, the light field display devices described above can operate in a similar way along direction Y, with a 2D array of pixels and a 2D pinholes array, or respectively, a 2D grid of reflecting surfaces, or a 2D lenslet array, for generating a 4D light field.

The light field display device enables to control the direction of rays coming from one point of an image. Thus, a light field display device enables to control the position and direction of each ray forming the light field without using additional lenses of variable focusing distance. As a result, we can display virtually an image at multiple distances using only a light field display device at a constant distance from the eyes of a subject. More precisely, the light field display device 60 enables to form an image at a controlled distance from the light field display device.

However, parallax barrier LFDs or lenslet array LFDs generally impose a trade-off between spatial and angular resolution.

The properties of light fields may be used for correcting a refractive error of a subject's eye.

Let us consider a light field of parallel beams generated using a light field display device of any type as mentioned above. The subject's eye is relaxed. A visual stimulus is displayed at infinity. In case the subject's eye is emmetrope, the image (for example of a point) formed by the emmetrope eye, through the cornea, the pupil and the crystalline lens, is focused on the subject's retina. Thus, the retinal image of a source point is focused on a point on the retina and perceived sharply. In contrast, in case the subject's eye is relaxed, but the eye is affected by myopia, the image (for example of a point) formed by the myopic eye (or shortsighted eye) is focused on a point in front of the subject's retina. Thus, for a myopic eye receiving a light field of parallel beams, the retinal image of the point extends over an area and is perceived blurred. For example, a light field display device may be used to generate a light field of divergent beams, so as to compensate for the aberration of the myopic eye. Then, when the myopic eye is relaxed, the image (for example of a point) formed by the myopic eye is focused on the subject's retina 19. Thus, the retinal image of the point is perceived sharply by the myopic subject.

Similarly, for a subject having a hypermetropic eye, which is relaxed, the image of a point formed using a light field with parallel beams is focused behind the subject's retina. Knowing the hypermetrope power value, it is possible to generate a light field of convergent beams so as to compensate for the aberration of the hypermetropic eye. Then, when the hypermetropic eye is relaxed, the image (for example of a point) of the LF with convergent beams formed by the hypermetropic eye is focused on the subject's retina. Thus, the retinal image of the point is perceived sharply by the hypermetrope subject.

More generally, knowing the refractive error of the eye, it is also possible to generate a light field which will be seen in focus by the eye. Using a light field display device, it is possible to generate a light field corresponding to different ocular aberrations along different directions, for example along X and Y directions. It is thus possible to compensate not only for spherical errors but also astigmatism, knowing the direction of the axis and the amount of astigmatism error (or cylinder) of the eye.

This could also include high order aberrations (HOA). The generated light field is thus optimized to form a sharp image on the retina (improved deconvolution with more degrees of freedom).

The present disclosure proposes to use light field display devices but instead of correcting or compensating a subject's eye defect, it proposes to inverse the problem and determine subjectively the refractive errors of a subject's eyes, in particular in binocular vision conditions, while enabling to differentiate the refraction properties of the right eye and left eye.

Device

To that end, we propose a light field display device capable of providing a different light field for the right eye and for left eye. According to the present disclosure, the light field display device displays to each eye an independent light field. This, in turn enables to perform binocular testing of the eyes while differentiating the right eye and the left eye refraction properties, without additional lenses.

FIG. 7 illustrates schematically a top view of a first embodiment of a system 100 for determining refraction features of both first and second eyes of a subject.

The system 100 of FIG. 7 comprises a light field display device 60, a control unit 80 and a system of localisation 6 of the respective positions of the first eye 1 and second eye 2 of a subject 10. In this application, the system of localisation 6 also determines the center of the pupil and the pupil diameter respectively of the first eye 1 and second eye 2. The system of localisation 6 enables to determine accurately which rays come into each eye.

The light field display device 60 may comprise a high definition screen combined with an array of pinholes or with a lenslet array as described above. Other types of light field display devices are contemplated without departing from the scope of the present disclosure.

On FIGS. 7, 8, 10 and 11, is shown a 3D orthogonal referential system, XYZ relative to the light field display device 60. Generally, the light field display device 60 comprises a screen surface located in an XY plane, the Z axis being orthogonal to the surface of the LFD 60.

The system of localisation 6 may comprise a camera and a time-of-flight sensor or a 3D sensor. Generally, the system of localisation 6 is attached to the light field display device 60. For example, the system of localisation 6 detects a first direction 7 and measures a first distance between the pupil center of the first eye 1 and the system of localisation 6. Similarly, the system of localisation 6 detects a second direction 8 and measures a second distance between the pupil center of the second eye 2 and the system of localisation 6. The system of localisation 6 and/or the control unit 80 deduce therefrom the respective position in three dimensions (3D) of the first eye 1 and of the second eye 2 of the subject relatively to the referential system (X, Y, Z) of the light field display device 60. The system of localisation 6 sends for example the position in 3D of the center of the pupil of the first eye 1 and, respectively, of the second eye 2, to the control unit 80. Advantageously, the system of localisation 6 measures the pupil diameter of the first eye 1 and, respectively, of the second eye 2 and/or the inter-pupillary distance between the first eye 1 and second eye 2. Then, the system of localisation 6 sends the measured pupil diameters and/or inter-pupillary distance to the control unit 80. The system of localisation 6 and/or the control unit 80 may also derive the distance between the light field display device 60 and the first eye 1, respectively, the second eye 2.

In short, the control unit 80 receives or deduces from the information transmitted by the system of localisation 6, the position in 3D of the first eye 1 and the position in 3D of the second eye 2 relatively to the referential system (X, Y, Z) of the light field display device 60.

Figure 8:
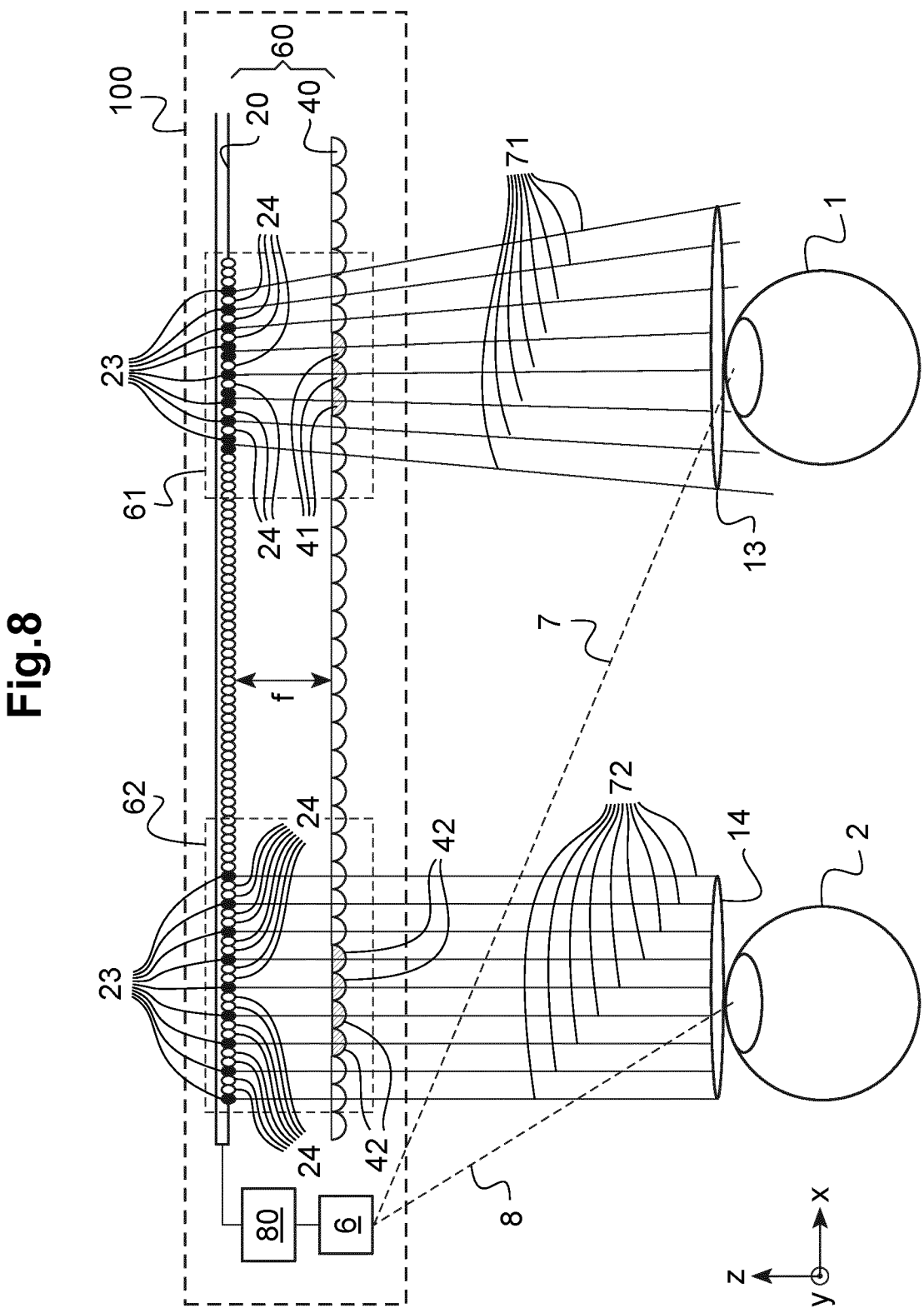

In the first embodiment, illustrated on FIGS. 7 and 8, the light field display device 60 comprises a first area 61 and a second area 62. The first area 61 and the second area 62 are spatially separated. The first area 61 and second area 62 are generated from a single display screen but correspond to distinct active pixels. Alternatively, the system includes two separate light field display devices: a first light field display device generate the first light field and a second light field display device generates the second light field. For example, in the case of a single display screen illustrated on FIG. 7, the first area 61 corresponds to the right half of the light field display device in front of the first eye 1 and the second area 62 corresponds to the left half of the light field display device in front of the second eye 2. More specifically, the control unit 80 addresses the first area 61 of the LFD 60 so as to generate a first light field 71 directed selectively toward the first eye 1 of the subject 10. The control unit 80 addresses the second area 62 of the LFD 60 so as to generate a second light field 72 directed selectively toward the second eye 2 of the subject 10. In that way, the first eye 1 does not receive the second light field 72, and the second eye 2 does not receive the first light field 71, without needing additional occultation means, such as an opaque wall in the sagittal plane of the subject between the two eyes and the light field display device. The first light field 71 is shaped so as to be received only by the first eye 1. Independently from the first light field 71, the second light field 72 is shaped so as to be received only by the second eye 2.

In monocular vision condition, the control unit 80 and LFD 60 may generate only one of the first light field 71 and the second light field 72. Alternatively, in monocular vision, the first light field 71 and the second light field 72 are generated simultaneously, one of the first eye 1 and the second eye 2 being occluded. For instance the non tested eye is occluded using one's hand or a card in front of the occluded eye. According to another alternative, the first or second light field is directed toward the non tested eye (in monocular exam), this light field being configured so as to illuminate the non tested eye with a blurred image and relax accommodation of the non tested eye.

In binocular vision conditions, the first embodiment enables to generate simultaneously the first light field 71 and the second light field 72, the two light fields being independent from each other.

In the example illustrated on FIG. 7, in binocular vision, the first eye 1 and the second eye 2 both stare a point far behind the screen of the LFD 60. FIG. 7 shows the first eye gaze direction 11, respectively second eye gaze direction 12, passing through the pupil center of the first eye 1, respectively second eye 2, and the virtual image of the point. For the far point, in order to have a natural binocular vision, we need to adjust the convergence with the distance of the target. Knowing the position of the eyes and the distance of the target, it is easy to calculate. The two light fields 71, 72 are generated to simulate a virtual target at a given distance, based on the natural convergence that is desired. For a point at infinite, the first eye gaze direction 11 and second eye gaze direction 12 are generally parallel to each other. In far vision, the virtual distance is comprised in a range from 4 m to infinity. Using current means, the virtual distance lies generally between 4 and 8 meters, for example 6 m, the first eye gaze direction 11 and second eye gaze direction 12 are slightly convergent. In near vision condition, the first eye gaze direction 11 and second eye gaze direction 12 are generally convergent on a same point or image. Moreover, the light field display device 60 can be configured so as to generate an image of a point corresponding to a lowered gaze direction in near vision or intermediate vision, combined with a predetermined convergence angle between the two eyes. More generally, any distance and direction may be tested using the light field display device 60.

FIG. 8 illustrates an example of a system 100 for determining refraction features of both eyes of a subject according to the first embodiment. The system 100 of FIG. 8 is based on light field display device 60 comprising a high resolution display screen 20 combined with a microlens array 40. By activating selectively some pixels 23, while other pixels 24 remain OFF, in the first area 61 and in the second area 62, the light field display device 60 generates two spatially separated light fields, the first light field 71 and the second light field 72 providing different refraction features for each eye. In the example shown, the first eye 1 being myopic, the first light field 71 provides a −1D spherical refraction correction, and the second eye 2 being emmetrope, the second light field 72 does not provide any refractive correction. Here, some pixels 23 are on while other pixels 24 are off, with different spacings between ON and OFF pixels and/or different patterns for ON and OFF pixels in the first area 61 and in the second area 62. This enables to generate simultaneously, for example, a first light field 71 of diverging beams toward the first eye 1 and a second light field 72 of parallel beams toward the second eye 2. The visual stimulus is produced simultaneously at a chosen distance by the first light field 71 and the second light field 72. The visual stimulus here is basically a point, for the first eye 1 and second eye 2, so as to permit fusion in binocular vision conditions.

On FIG. 8 are represented a first, respectively second, eye motion box 13, respectively 14. The eye motion box 13, respectively 14 corresponds to the zone where the first eye 1, respectively second eye 2, can see the stimulus. The eye motion boxes 13, 14 are spatially limited so that first eye 1 sees only the first stimulus generated by the first area 61, while the second eye 2 sees only the second stimulus generated by the second area 62. On FIG. 8, three microlenses 41 in the first area 61 provide the first light field coming into the first eye 1 pupil and four other microlenses 42 in the second area 62 provide the second light field coming into the second eye 2 pupil.

Figure 9:
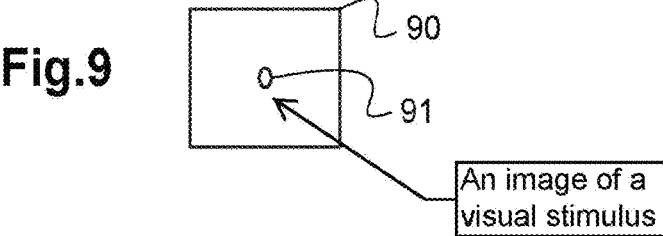

FIG. 9 illustrates an exemplary visual stimulus as seen by the subject in binocular vision conditions, as illustrated on FIG. 8. The two retinal images are fused which enables the subject 10 to see the image of the point 91 sharply in the field of view 90 of the subject with a different and appropriate refraction correction for each eye. The image of the stimulus is formed by superposition or fusion of the first stimulus and second stimulus. For example, the image of the stimulus appears as a luminous point on a black background.

FIG. 10 illustrates schematically a top view of a second embodiment of a system 100 for determining refraction features of both first and second eyes 1, 2 of a subject 10. Instead of using two separate areas 61, 62 of the light field display device 60, a same light field area 63 is used for generating the first light field 71 and second light field 72. In the second embodiment, the first light field 71 and the second light field 72 are generated by temporal alternation or, in other words sequentially. In a variant of the second embodiment, the first light field 71 and second light field 72 may be generated using partially overlapping areas of the light field display device.

Similarly as in the first embodiment, the system of localisation 6 determines the positions of the first eye 1 and of the second eye 2 which enables the control unit 80 and the light field display device 60 to direct the first light field 71 selectively toward the first eye 1 and the second light field 72 toward the second eye 2 of the subject 10.

In monocular vision conditions, for the second embodiment, only one of the first and second light fields is generated at a time. Thus, only one eye receives a light field directed selectively toward this eye, without the need for any occultation means.

In binocular vision, for the second embodiment, the first light field 71 and the second light field 72 are generated alternatively but with a fast temporal alternation. In other words, the first light field 71 and the second light field 72 are generated with an alternation frequency higher than a threshold comprised between 20 hertz and 120 hertz so as to enable fusion of the images seen by the two eyes. For instance, the stimulus may be an optotype.

Process

We will now describe how the system 100 for determining refraction features of both first and second eyes of a subject can be used to perform an eye exam. Refraction is just a part of a more global eye exam, we will focus here on the refraction part in far vision and optionally in near vision.

A system 100 for determining refraction features of both first and second eyes of a subject according to any of the embodiments described above is used to generate independent light fields directed selectively toward each eye. The processes disclosed enable to determine the appropriate refraction correction for each eye independently, whether in monocular or in binocular vision conditions, and without additional lenses.

The light field display device 60 is positioned in front of the eyes of the subject. The working distance, or in other words, the distance between the subject's eyes and the surface of the light field display device 60, may be very different depending on the type of light field display device. Some light field display devices are designed for very short working distance, for example 5 mm to 50 mm for AR/VR applications. Other light field display devices are designed for short to medium working distance, for example from 300 mm to 600 mm, for smartphone or tablet. Still other light field display devices may be designed for long working distance for example in TV-like use (2-5 m).

For far vision refraction measurement, it is important to display a virtual image close to the infinity to reduce accommodation, independently from the physical position of the light field display device. This virtual image of a stimulus is also formed by the light field display device.

According to the present disclosure, to generate the appropriate light field directed toward each eye selectively, it is necessary to know with accuracy the pupil diameter and the position of each eye in the referential system of the light field display device. The pupil diameter and position are used to estimate which rays generated by the light field display devices are useful to reach the eye pupil, and which rays are not useful. It can be done using a camera and time-of-flight sensor or using a 3D sensor of a localisation system 6, as disclosed above.

As described in relation with FIGS. 7, 8 and 10, the system 100 for determining refraction features of both first and second eyes of a subject is adapted to generate at least two independent light fields, i.e. one light field for each eye simultaneously or in time multiplexing. This setup enables to address two separate images, one image for each eye and two different corrections, i.e. a specific refraction correction for each eye.

Each light field 71, 72 is generated for a specific correction for example sphere (Sph), cylinder and axis (Cyl and Axis), and eventually high order aberrations (HOA). Each light field 71, 72 is generated as a function of the pupil diameter considered, the distance between the light field display device and the eye, the distance between the targeted virtual image and the eye, the characteristics of the screen and the targeted image on the retina. For example, the light field may be simulated using different models are based on ray-tracing. For an expected picture on the retina, the ray-tracing model is used to back-propagate all the rays forming the image for a given defect of the eye up to the LFD and select the corresponding generated rays.

As an illustration, we detail herein a process to determine refraction in far vision.

The process comprises generally several phases labelled A, B and C, detailed below. For phase A and phase B (separately), the test is performed in monocular vision conditions for the left eye or the right eye and then phase A+B is performed for the other eye. For phase C, the test is performed in binocular vision conditions.

During monocular exam, occultation of the non-tested eye may be necessary. During the phases A and B, it is possible to have a light field illuminating both eyes and to occlude one eye (the eye for which the measurement of refraction, Rx, is not done), using for instance one's hand, or a card in front of the occluded eye.

Alternatively, it is possible to have a light field illuminating only the measured eye, the other eye not perceiving the light field but only a dark background.

Alternatively again, another light field may illuminate the non-tested eye, said another light field generating a blurred retinal image on the non-tested eye to relax accommodation.

According to still another alternative, a first light field is displayed as a first image to the first eye and a second light field is displayed as a second image to the second eye. More precisely, the first light field generates a first retinal image on the first eye and the second light field generates a second retinal image on the second eye. The first light field and the second light field have a part, in general in periphery, of the first and second image common to both eyes which is seen by both eyes. For testing the first eye, only the first light field comprises a specific part, generally in its center, comprising for example an image of optotypes, while the center of the second light field is empty or has no specific part or has a significantly reduced contrast. The central part is switched between the first light field and the second light field for testing the second eye, the common part in periphery remaining the same. The combination of the first light field and second light field enables to simulate a common 3D object in the common part of the images. This combination provides accommodation of the first and second eyes at a determined virtual distance corresponding to the common part of the first and second images. Moreover, since only one of the first light field or the second light field has another, generally central, part of the first or second image, this specific part is seen only by the tested eye. Thus, refraction of a single eye may be tested, while forcing accommodation of the two eyes at a predetermined accommodation distance.

Phase A. Search of the Sphere (Monocular)

It is proposed to apply and adapt a fog-method. This well-known method consists in adding a refraction power (for example +1.50 D) to the initial refraction value, in order to form the image in front of the retina. It enables to relax accommodation. The initial refraction value is generally comprised between −20 D and +20 D. The initial refraction value is generated by the light field display device without additional lens. The additional fog value (for ex. +1.5 D) is also generated by the light field display device without additional lens. The image is seen blurred with a low visual acuity. Then the process is to use only the light field display device to reduce this additional sphere step by step, for example of 0.25 D and find the best acuity and stop when acuity is not improving. The sphere value is the highest value giving the maximal acuity.

The light field display device is used to simulate a fog process on one eye. The initial refraction, noted (S0, C0, A0), may be determined from a previous refraction exam or obtained by another objective method, where S0 stands for an initial refractive value, C0 an initial cylinder value and A0 an initial axis value. The light field display device generates a light field corresponding to a refraction of (S0+ΔS, C0, A0) where ΔS represents a variable refraction. ΔS is initially set to +1.50 diopter so as to generate a blurred image of the retina and relax accommodation. Then, the light field is modified so as to decrease ΔS by steps and improve acuity until a best sphere value is determined. The best sphere value generally corresponds to the first image seen sharply by the subject. Using the light field display device, steps are not necessary 0.25 D. Steps of ΔS can be lower than 0.25 D. For example, in the case of a light field display device comprising a display screen combined with a parallax barrier or with a lenslet array, as illustrated on FIGS. 5 and 6, the minimum step of ΔS depends on the pixel pitch, p, of the display screen 20 and on the pinhole pitch or microlens pitch, Δx. If the refraction is purely spherical, this phase A is equivalent to changing the distance of the virtual image generated by the light field display device.

Complete Search of the Sphere if No Initial Value

In this case, the light field display device is used to simulate a Badal optometer. In other words, the light field display device is used to generate a virtual image coming closer to the eye and stop when the image can be seen sharp, it gives a first estimation of the spherical equivalent (SE=S+ C/2). The image may be an optotype with fine details or a patterned image for example.

FIG. 11 illustrates an example with a light field display device 60 at a distance of 500 mm from the eye 1 of a subject. The light field display device is configured to generate a light field corresponding to +10 D spherical refraction, or, in other words, 100 mm behind the eye 1, so that the virtual image 51 is at 600 mm in front of the light field display device 60. This distance is progressively increased to the infinity (position 52) and then the virtual image is behind the screen (position 53) until being again in front of the LFD (position 54) between 0 and 400 mm. The process stop at the first position really sharp, the corresponding distance d enables to determine the best sphere value S using the simple relation S=−1/d.

This method enables to relax accommodation, even if the subject's refraction is unknown, while maintaining the same visible size of the image at the different virtual distances, according to the principle of a Badal optometer.

Phase B. Search of the Cylinder (Monocular)

The light field display device is used to determine the axis value using a method equivalent to the cross-cylinder.

Let us consider a light field display device 60 generating a light field 71 toward an eye 1 of the subject 10. In this case, the light field 71 corresponds to diverging or converging rays simulating a spherical refraction S0 and a cylindrical refraction C0 relatively to an axis A0. The image generated may correspond to an optotype or to a cloud of black dots. Generally, the spherical refraction S0 is determined as disclosed in phase A in far vision at the best SE found in phase A.

The phase B of the exam consists in changing the original axis of the cylinder from the initial value (S0, C0, A0) and presenting the image of a same source with two different axis values to the same eye 1: A0+AA and A0−AA (AA is depending of A0 and the value of the selected Cross Cylinder 0.25D or 0.50D). If A0 is the best value, the subject perceives the two images with the same level of blur. If not, A0 is changed to A in the preferred direction. Two images are presented to the same eye one with A+ΔA and the other with A−ΔA, until the subject perceives the two images as having the same level of blur.

According to an exemplary embodiment, the light field display device presents alternately the two different axis values (one image corresponding to A+ΔA and the other to A−ΔA) to the same eye, with an alternation frequency low enough so that the subject can perceive the change in the light field displayed and compare their respective level of blur.

According to another exemplary embodiment, two different areas of the light field display device are used to generate simultaneously two images corresponding to the two different axis values toward the same eye.

FIG. 12 illustrates an example of two images 93, 94 generated side by side in the field of view 90 of the subject 10 in monocular vision. For example, image 93 corresponds to an area with a (S0, C0, A0+ΔA) correction and image 94 corresponds to an area with a (S0, C0, A0−ΔA) correction. This enables the subject to compare and determine if the two images 93, 94 have the same level of blur.

The light field display device is then used to determine the cylinder value using a method equivalent to a cross-cylinder.

This step of the exam consists in changing the original value of the cylinder from the initial values (S0, C0, A0) and presenting two different values: C0+ΔC and C0−ΔC. If C0 is the best value, the subject perceives the two images with the same level of blur. If not, C0 is changed to C in the preferred direction. Two images are presented to the same eye one with C+ΔC and the other with C−ΔC, until the subject perceives the two images as having the same level of blur.

According to an exemplary embodiment, the light field display device presents alternately the two different cylinder values (one image corresponding to C+ΔC and the other to C−ΔC) to the same eye.

According to another exemplary embodiment, two different areas of the light field display device are used to generate simultaneously two images corresponding to the two different cylinder values toward the same eye.

FIG. 13 illustrates an example of two images 95, 96 generated side by side in the field of view 90 of the subject 10 in monocular vision. For example, image 95 corresponds to an area with a (S0−ΔC/2, C0+ΔC, A0) correction and image 96 corresponds to an area with a (S0−ΔC/2, C0−ΔC, A0) correction. The sphere value is changed to S0−ΔC/2 to operate at a constant SE. This enables the subject to compare and determine if the two images 95, 96 have the same level of blur.

Alternatively, the light field display device is used to determine the axis and cylinder values at the same time.

The light field display device is configured to display simultaneously N different corrections. For example, light field display device generates a plurality of images corresponding to different corrections changing axis and cylinder values at the same time.

The initial values are defined here in a J0/J45 referential: [C0*cos(2*A); C0*sin(2*A)]=[X0; Y0].

The light field display device generates four images corresponding to four different choices: [X0+δ; Y0], [X0−δ; Y0], [X0; Y0−δ] and [X0; Y0−δ] where δ is a small step in diopters.

For each value of δ, the subject determines the preferred direction, or, in other words, the image which is the less blurred among the four choices.

Alternatively, the four different choices may correspond to the following: [X0+δ/√2; Y0+δ/√2], [X0−δ/√2; Y0−δ/√2], [X0−δ/√2; Y0+δ/√2], [X0+δ/√2; Y0−δ/√2].

In another example, the light field display device generates six images corresponding to six different choices:

[X0+δ*cos(0); Y0+δ*sin(0)], [X0+δ*cos(60°); Y0+δ*sin(60°)],

[X0+δ*cos(120°); Y0+δ*sin(120°)], [X0+δ*cos(180°); Y0+δ*sin(180°)],

[X0+δ*cos(240°); Y0+δ*sin(240°)]/[X0+δ*cos(300°); Y0+δ*sin(300°)].

For each value of δ, the subject determines the preferred direction, or, in other words, the image which is the less blurred among the six choices.

Alternatively, in the case of multiple choices, the subject's response may be collected automatically as a function of the gaze direction detected, using for example an eye-tracker or a camera of the localisation system 6. Generally, the level of sphere S is adjusted by +0.25D for each cylinder value of −0.50D added.

Other methods can be used to determine axis and cylinder values. In particular, a complete search is performed if no initial value is known. For example, the light field display device generates a light field with a continuous variation of a small cylinder (from 0.5D to 1.0D) along a variable axis from 0 to 180 degrees and the process is stops when the subject determines the best focus position. Alternatively, a fixed cylinder value (0.5D) is tested in four main directions as in a four-quadrant method.

The light field display device may also be used for checking of the sphere. For example by displaying two images sequentially or simultaneously, one with adding +0.25D and the other −0.25D to the sphere value found, it is possible to check that the sphere found is the maximum value that gives the best acuity.

Phase C. Binocular Optimization and Check

First, the light field display device generates a separate view of the same test for each eye, in bi-ocular vision conditions. For example a common part on the two images is used to have fusion of the images, while a letter is used only for the left eye and the same letter is placed at another position for the right eye. The subject compares the sharpness. If the sharpness of the two views is different, the balance of the two spheres may be determined. This test is performed in far vision, and at the beginning with the monocular refraction for each eye.

Here, the light field display device generates two light fields of the same image with the two refractive errors found previously in monocular vision for the right eye (SR, CR, αR) and for the left eye (SL, CL, αL). This step enables to compare the sharpness of the images seen by the two eyes in a same state of accommodation. Then, the light field display device generates light fields with an additional sphere, of +0.5D for example, to both eyes. The subject is asked to compare the blur level of the two images. If the level of blur is the same, no balance is needed. If the level of blur is not the same, it is necessary to add +0.25D or +0.50D to the eye seeing the image less blurry, in order to balance the two eyes. Then, the sphere values of the two eyes are decreased by step of −0.25 D in order to reach the maximal acuity.

Then, the light field display device is used for binocular or stereo testing.

Conventional tests for binocular vision are generally performed by dissociating images directed to the right eye and left eye, for example using prisms, coloured filters and/or polarized tests.

The ability of the light field display device to display two separate light fields for left eye and right eye, respectively is used here to check the stereoscopic performance with the refraction.

More precisely, with an image at the infinity, last test and adjustment of +/−0.25D. An additional sphere of +0.25 D to both light fields should blur the binocular vision whereas an additional sphere value of −0.25 D should change nothing to the binocular vision.

The light field display device may also be used for the determination of the refraction in near vision. For example, a method is based on the evaluation of the accommodation range of the subject. The light field display device is configured to display an image at different distances, with the refraction correction found in far vision. The shortest distance where the visual acuity is kept, corresponds to the accommodation range. In general, the addition needed in near vision is about ⅔ of the accommodation range in diopter.

Thus, the same light field display device enables to determine refraction in near vision.

Although representative processes and articles have been described in detail herein, those skilled in the art will recognize that various substitutions and modifications may be made without departing from the scope of what is described and defined in the appended claims.

The invention claimed is:

1. A system for determining refraction features of both first and second eyes of a subject, the system comprising:

a light field display device having a reference frame in three-dimensions;

a system of localisation of 3D positions of the first and second eyes of the subject viewing said light field display device, relatively to the reference frame; and control circuitry configured to control the light field display device, wherein the control circuitry and the light field display device are configured to use the 3D position of the first eye relatively to the reference frame to generate a first light field directed selectively toward the first eye of the subject, said first light field being adapted to form a first image on the first eye of the subject, wherein the control circuitry is further configured to adjust said first light field as a function of at least a first refraction parameter associated with at least a first optical aberration for said first eye so that said first image is perceived corrected for a first adjusted value of said first refraction parameter by the first eye, wherein the control circuitry is further configured to determine a refraction feature of the first eye from the first adjusted value of said first refraction parameter, wherein the control circuitry and the light field display device are configured to use the 3D position of the second eye relatively to the reference frame to generate a second light field directed selectively toward the second eye of the subject, said second light field being adapted to form a second image on said second eye of the subject, wherein the control circuitry is further configured to adjust said second light field as a function of at least a second refraction parameter associated with at least a second optical aberration for the second eye so that the second image is perceived corrected for a second adjusted value of said second refraction parameter by the second eye, and wherein the control circuitry is further configured to determine a refraction feature of the second eye from the second adjusted value of said second refraction parameter.

2. The system according to claim 1, wherein the light field display device comprises a single screen, and wherein the first light field and the second light field are generated from a same area or from two distinct areas of the light field display device.

3. The system according to claim 1, wherein the light field display device comprises a first screen adapted to generate the first light field directed selectively toward said first eye of the subject and a second screen adapted to generate the second light field directed selectively toward the second eye of the subject.

4. The system according to claim 1, further comprising:

a user interface adapted to record a first response of the subject relative to a first sharpness of the first image perceived by the first eye and a second response of the subject relative to a second sharpness of the second image perceived by the second eye, wherein the control circuitry is further configured to adjust respectively said first and second light fields as a function of said first and second responses recorded.

5. The system according to claim 4, wherein the user interface is adapted to enter values of said first and second refraction parameters, and wherein the control circuitry is further configured to adjust respectively said first and second light fields as a function of said first and second refraction parameters values entered.

6. The system according to claim 1 further comprising:

means for selectively occluding the first light field toward the first eye and/or means for selectively occluding the second light field toward the second eye.

7. The system according to claim 1, wherein the light field display device comprises a digital display comprising an array of pixels and a parallax barrier mask layered on the array of pixels.

8. The system according to claim 1, wherein the system of localisation comprises an eye tracker, a 3D scanning device, a camera, a time-of-flight sensor and/or a pupil-size measuring device.

9. The system according to claim 1, wherein the system of localisation is adapted to determine an eye gaze direction.

10. The system according to claim 1, wherein the first light field and the second light field are predetermined so that the first image comprises a visual stimulus and the second image comprises said visual stimulus, enabling fusion of the first image and the second image by the subject.

11. A method for determining a refraction feature of both eyes of a subject, the method comprising:

(a) localising a 3D position of a first eye and a 3D position of a second eye of the subject relatively to a three-dimensions reference frame of a light field display device;

(b) using a control circuitry and the light field display device to generate, using the localised 3D position of the first eye relatively to the three-dimensions reference frame, a first light field directed selectively toward the first eye of the subject, said first light field being adapted to form a first image on said first eye of the subject;

(c) adjusting the first light field as a function of at least a first refraction parameter associated with at least a first optical aberration of the first eye so that said first image is perceived corrected for a first adjusted value of said first refraction parameter by the first eye;

(d) determining a refraction feature of the first eye from the first adjusted value of said first refraction parameter;

(e) using the control circuitry and the light field display device to generate, using the localised 3D position of the second eye relatively to the three-dimensions reference frame, a second light field directed selectively toward the second eye of the subject, said second light field being adapted to form a second image on the second eye of the subject;

(f) adjusting the second light field as a function of at least a second refraction parameter associated with at least a second optical aberration of the second eye so that the second image is perceived corrected for a second adjusted value of said second refraction parameter by the second eye; and (g) determining a refraction feature of the second eye from the second adjusted value of said second refraction parameter.

12. The method according to claim 11, wherein steps (b) to (c) and, respectively, steps (e) to (f) are performed sequentially in time and wherein during steps (b) to (c) the second light field is off or occluded toward the second eye and wherein during steps (e) to (f) the first light field is off or occluded toward the first eye.

13. The method according to claim 11, wherein steps (b) to (c) and, respectively, steps (e) to (f) are performed simultaneously.

14. The method according to claim 11, further comprising a run in which steps (b) to (c) and, respectively, steps (e) to (f) are performed sequentially in time and, during steps (e) to (f), the first light field is off or occluded toward the first eye for the first eye in monocular vision and another run in which steps (b) to (c) and, respectively, steps (e) to (f) are performed sequentially in time and, during steps (b) to (c), the second light field is off or occluded toward the second eye for the second eye in monocular vision and a run in which steps (b) to (c) and, respectively, steps (e) to (f) are performed simultaneously for the first eye and the second eye in binocular vision.

15. The method according to claim 11 further comprising:

(h) recording a first response of the subject relative to a first sharpness of the first image perceived by the first eye, and (i) recording a second response of the subject relative to a second sharpness of the second image perceived by the second eye, wherein during step (c) the first light field is adjusted as a function of said first response recorded during step (h), and wherein during step (f) the second light field is adjusted as a function of said second response recorded during step (i).

16. The system according to claim 2, wherein the light field display device comprises a digital display comprising an array of pixels and a parallax barrier mask layered on the array of pixels.

17. The system according to claim 3, wherein the light field display device comprises a digital display comprising an array of pixels and a parallax barrier mask layered on the array of pixels.

18. The system according to claim 4, wherein the light field display device comprises a digital display comprising an array of pixels and a parallax barrier mask layered on the array of pixels.

19. The system according to claim 5, wherein the light field display device comprises a digital display comprising an array of pixels and a parallax barrier mask layered on the array of pixels.

20. The system according to claim 6, wherein the light field display device comprises a digital display comprising an array of pixels and a parallax barrier mask layered on the array of pixels.

\* \* \* \* \*